US009068576B2

(12) United States Patent
Plante et al.

(10) Patent No.: US 9,068,576 B2
(45) Date of Patent: Jun. 30, 2015

(54) DEVICE FOR ORIENTING AN OBJECT ACCORDING TO A GIVEN SPATIAL ORIENTATION

(75) Inventors: Jean-Sébastien Plante, Sherbrooke (CA); Geneviève Miron, Longueuil (CA); Sylvain Proulx, Sherbrooke (CA); Patrick Chouinard, Sherbrooke (CA); Alexandre Girard, Sherbrooke (CA); Jean-Philippe Lucking Bigué, Orford (CA)

(73) Assignee: SOCPRA SCIENCES ET GINIE S.E.C., Sherbrooke, Quebec (CA)

( * ) Notice: Subject to any disclaimer, the term of this patent is extended or adjusted under 35 U.S.C. 154(b) by 379 days.

(21) Appl. No.: 13/207,599

(22) Filed: Aug. 11, 2011

(65) Prior Publication Data

US 2012/0041252 A1 Feb. 16, 2012

Related U.S. Application Data

(60) Provisional application No. 61/373,046, filed on Aug. 12, 2010.

(30) Foreign Application Priority Data

Aug. 12, 2010 (CA) .................................. 2713053

(51) Int. Cl.
  *A61N 5/00* (2006.01)
  *A61N 5/01* (2006.01)
  (Continued)

(52) U.S. Cl.
  CPC ............. *F15B 15/00* (2013.01); *Y10T 29/4998* (2015.01); *A61M 37/0069* (2013.01);
  (Continued)

(58) Field of Classification Search
  CPC ........ F15B 15/00; F15B 15/02; F15B 15/202; F15B 15/204; A61N 5/1001; A61N 5/1002; A61N 5/1007; A61N 5/1014; A61N 5/1016; A61N 2005/1003; A61N 2005/1008

USPC ....................................................... 600/1, 3–7
See application file for complete search history.

(56) References Cited

U.S. PATENT DOCUMENTS 4,976,582 A    12/1990 Clavel
5,080,020 A *   1/1992 Negishi ...................... 104/138.2
(Continued)

FOREIGN PATENT DOCUMENTS

DE       19963194 A1    7/2001
WO      WO0192971 A2   12/2001

OTHER PUBLICATIONS

Pelrine et al., Applications of Dielectric Elastomer Actuators, Smart Structures and Materials 2001: Electroactive Polymer Actuators and Devices, Yoseph Bar-Cohen, ed., SPIE Proceedings vol. 4329 (Mar. 5-8, 2001), p. 335-349.*

(Continued)

*Primary Examiner* — Charles A Marmor, II
*Assistant Examiner* — Thaddeus Cox
(74) *Attorney, Agent, or Firm* — Pearl Cohen Zedek Latzer Baratz LLP

(57) ABSTRACT

There is disclosed a device for orienting an object according to a given spatial orientation. The device comprises a frame and a supporting member connected to the frame and adapted for supporting at least a portion of the object. The device for orienting an object comprises a plurality of fluid actuated devices for displacing the supporting member with respect to the frame. Each of the fluid actuated devices is actuatable between a first position wherein the device has a first length and a second position wherein the device has a second length. The device for orienting comprises an actuation mechanism comprising a plurality of actuating valves for actuating the corresponding fluid actuated device; wherein an actuation of at least one of the fluid actuated devices enables to displace the supporting member with respect to the frame, thereby orienting the object according to the given spatial orientation. The device for orienting may be of particular interest in the medical sector as a medical object manipulator for reaching a given target in an anatomical structure with a suitable accuracy, for example in the treatment and/or diagnosis of prostate cancer.

19 Claims, 11 Drawing Sheets

(51) Int. Cl.

| | | |
|---|---|---|
| *A61M 36/00* | (2006.01) | |
| *A61M 36/04* | (2006.01) | |
| *F15B 15/00* | (2006.01) | |
| *F15B 15/02* | (2006.01) | |
| *A61M 37/00* | (2006.01) | |
| *A61N 5/10* | (2006.01) | |
| *F16B 15/00* | (2006.01) | |
| *B29C 31/00* | (2006.01) | |
| *F16K 31/02* | (2006.01) | |
| *A61M 36/10* | (2006.01) | |
| *F15B 15/10* | (2006.01) | |

(52) U.S. Cl.
CPC ............ *A61N 5/1027* (2013.01); *F15B 15/103* (2013.01); *F16B 15/00* (2013.01); *B29C 31/008* (2013.01); *F16K 31/02* (2013.01)

(56) References Cited

U.S. PATENT DOCUMENTS

| | | | |
|---|---|---|---|
| 5,144,848 A * | 9/1992 | Uenishi et al. | ................ 73/866.5 |
| 5,484,219 A | 1/1996 | Drew et al. | |
| 2002/0111634 A1 | 8/2002 | Stoianovici et al. | |
| 2003/0120283 A1 | 6/2003 | Stoianovici et al. | |
| 2003/0221504 A1 | 12/2003 | Stoianovici et al. | |
| 2004/0148974 A1 | 8/2004 | Stoianovici et al. | |
| 2006/0058640 A1 * | 3/2006 | Cinquin et al. | ................ 600/415 |
| 2007/0034046 A1 | 2/2007 | Stoianovici et al. | |
| 2007/0034047 A1 | 2/2007 | Stoianovici et al. | |
| 2008/0097413 A1 * | 4/2008 | Ostojic | ............................ 606/1 |
| 2008/0161830 A1 | 7/2008 | Sutherland et al. | |
| 2009/0149867 A1 | 6/2009 | Glozman et al. | |
| 2009/0247993 A1 | 10/2009 | Kirschenman et al. | |
| 2009/0326364 A1 | 12/2009 | Goldenberg et al. | |
| 2010/0041938 A1 * | 2/2010 | Stoianovici et al. | ............. 600/7 |

OTHER PUBLICATIONS

Krivts, Igor L.; Krejnin, German V., Pneumatic Actuating Systems for Automatic Equipment, CRC Press, Taylor & Francis Group, Boca Raton, FL, 2006.

Yang, W.H.; Feng, W.W., On Asymmetrical Deformations of Nonlinear Membranes, Transactions of the ASME, Series E, Journal of Applied Mechanics, 37(4), pp. 1002-1011.

International Search Report for International Application No. PCT/CA2011/000920 mailed Nov. 25, 2011.

\* cited by examiner

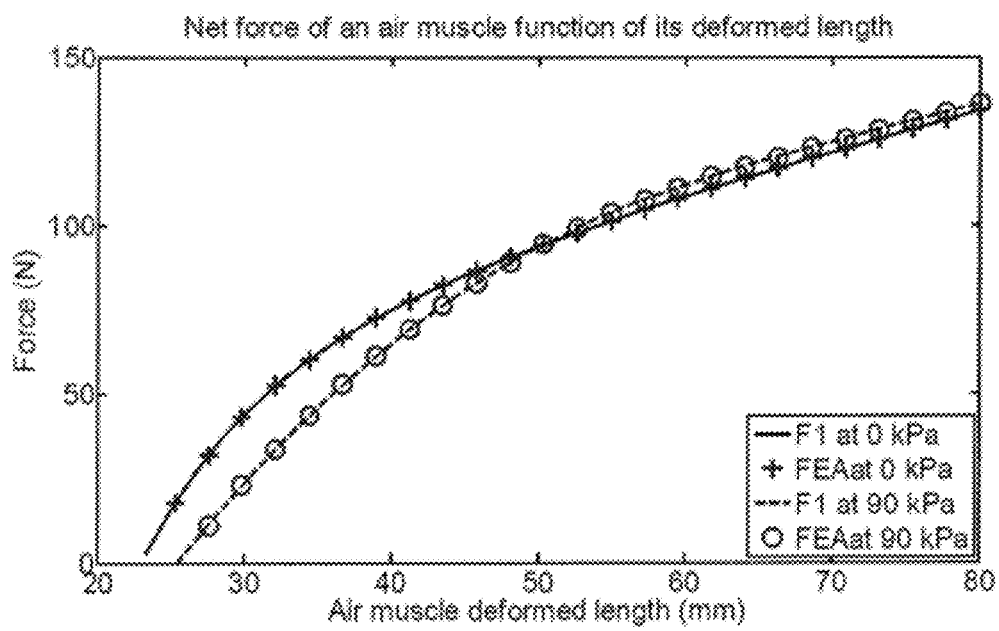
FIGURE 7: FEA ON A MUSCLE COMPARED TO ANALYTICAL RESULTS (r0: 12.1 mm; H: 23 mm; C1: 165kPa; C2: 245 kPa; h: 1 mm).
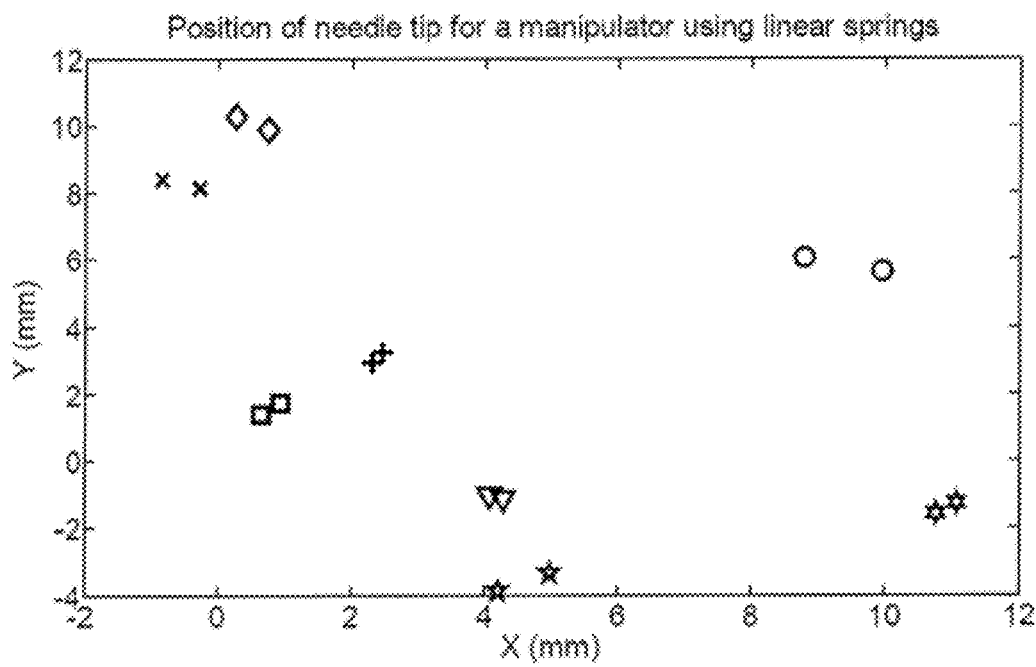
FIGURE 8: PREDICTED VS EXPERIMENTAL POSITION OF NEEDLE TIP OF A LINEAR SPRING MANIPULATOR

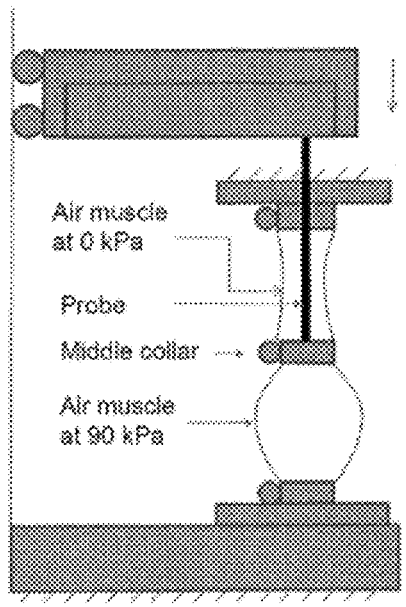
FIGURE 9
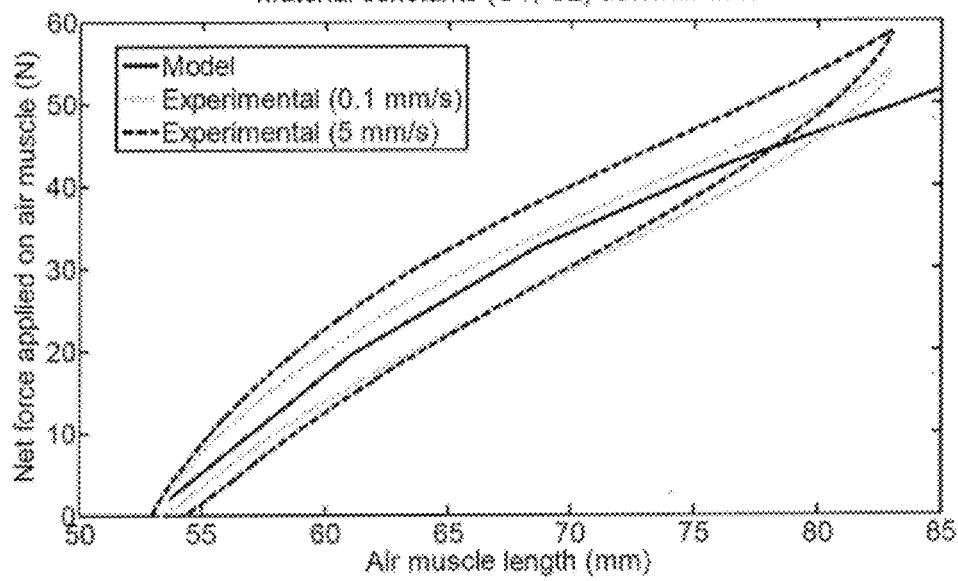
FIGURE 10: (r0: 12.1 mm; H: 53 mm; C1: 155kPa; C2: 175 kPa; h: 1 mm) WITHOUT PRESSURE.

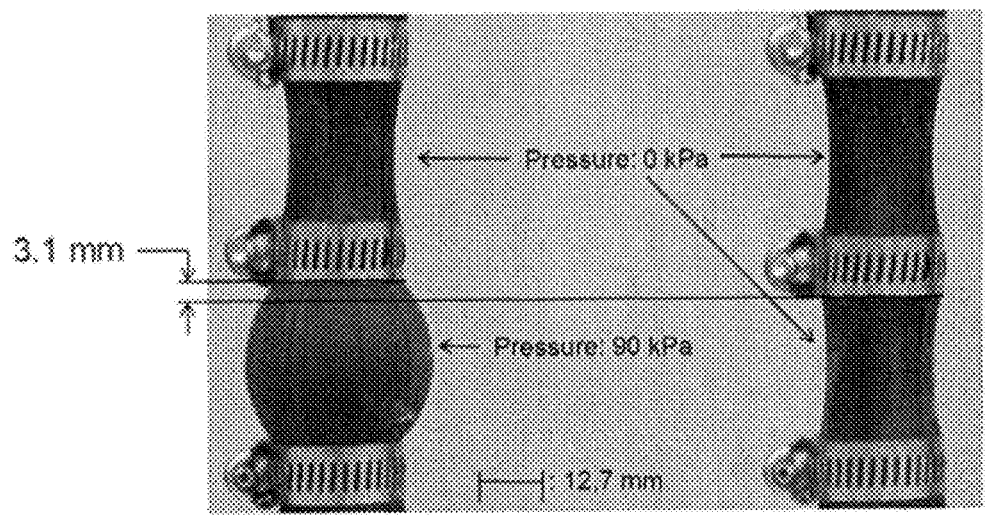
FIGURE 11 : (r0: 12.1 mm; H: 23 mm; C1: 155kPa; C2: 175 kPa; h: 1 mm)
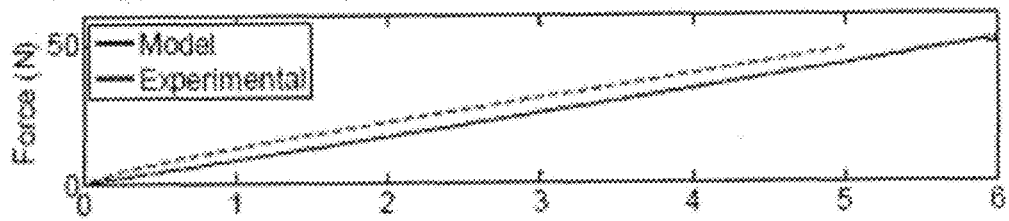
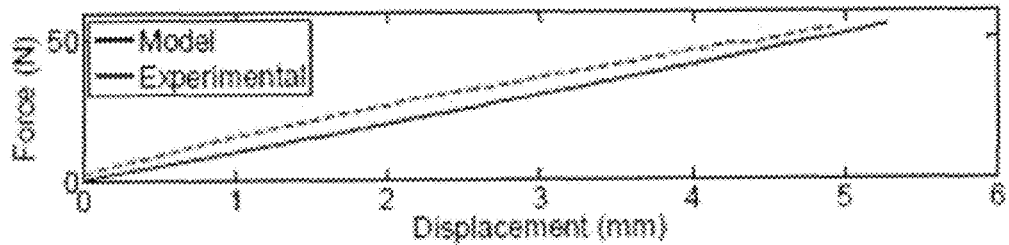
FIGURE 12 : FORCE IS APPLIED TOWARD THE LOWER ACTUATOR ON FIGURE 11 AT A SPEED OF 0.1 mm/s.

| SYSTEM PARAMETER | VALUE |
|---|---|
| OUTER FRAME RADIUS (Rs) | 80 mm |
| DISTANCE BETWEEN PLANES (dp) | 180 mm |
| NEEDLE SUPPORT RADIUS (Rn) | 20 mm |
| DISTANCE FROM PLANE 2 TO NEEDLE TIP (dt) | 575 mm |

FIGURE 13A : SYSTEM DIMENSIONS

| INITIAL LENGTH H (mm) | 1 | 2 | 3 | 4 | 5 | 6 |
|---|---|---|---|---|---|---|
| PLANE 1 | 30 | 42 | 37 | 32 | 37 | 42 |
| PLANE 2 | 40 | 34 | 37 | 40 | 37 | 40 |

FIGURE 13B : AIR MUSCLE INITIAL LENGTH (H)

| AIR MUSCLE PARAMETERS | DIMENSION |
|---|---|
| INITIAL RADIUS (r0) | 30 mm |
| WALL THICKNESS (h) | 3 mm |
| MATERIAL CONSTANT C1 | 185 kPa |
| MATERIAL CONSTANT C2 | 215 kPa |
| ACTUATION PRESSURE (P) | 180 kPa |

FIGURE 13C : AIR MUSCLE DIMENSIONS

| PARAMETER | AVERAGE POSITIONNING ERROR (mm) | STANDARD DEVIATION (mm) |
|---|---|---|
| INITIAL LENGTH (H) | 2.9 | 0.3 |
| MATERIAL CONSTANT (C1, C2) | 1.4 | 0.5 |
| PRESSURE (P) | 1.8 | 1.2 |
| INITIAL RADIUS (r0) | 1.9 | 0.7 |
| WALL THICKNESS (h) | 3.1 | 0.3 |

FIGURE 18A : SENSITIVITY ANALYSIS OF THE AIR MUSCLE POSITIONNING MODEL

| PARAMETER | AVERAGE POSITIONNING ERROR (mm) | STANDARD DEVIATION (mm) |
|---|---|---|
| ACTUATION DISPLACEMENT | 0.6 | 0.2 |
| SPRING STIFFNESS | 2.7 | 0.2 |
| SPRING FREE LENGTH | 2.9 | 0.1 |

FIGURE 18B : SENSITIVITY ANALYSIS OF THE LINEAR SPRING

DEVICE FOR ORIENTING AN OBJECT ACCORDING TO A GIVEN SPATIAL ORIENTATION

CROSS REFERENCE TO RELATED APPLICATIONS

This application claims priority of U.S. Provisional Patent Application Ser. No. 61/373,046 filed on Aug. 12, 2010 and entitled "device and integrated device for orienting an object according to a given spatial orientation", the specification of which is hereby incorporated by reference.

This application also claims priority of Canadian Patent Application serial number 2,713,053 filed on Aug. 12, 2010 and entitled "device for orienting an object according to a given spatial orientation", the specification of which is hereby incorporated by reference.

FIELD OF THE INVENTION

The invention generally relates to the placing and the orientation of an object and more particularly relates to a device for orienting an object according to a given spatial orientation. The device may have several applications such as in the medical field for providing a needle manipulator for example. The device may be used for reaching a given target in an anatomical structure with a suitable accuracy, for example in the treatment and/or diagnosis of prostate cancer.

BACKGROUND OF THE INVENTION

Robot-assisted techniques are today widely used in the medical sector, for example for intervention and diagnosis purposes.

Magnetic Resonance Imaging (MRI) and other various imaging techniques are also used for early diagnostic of cancers since MRI may help improving tumor perceptibility, while helping to target smaller tumor during biopsy.

Even if imaging techniques are well suited for detecting most of tumors, biopsies are generally still required for analyzing the malignancy of the tumor.

For example, a TransRectal UltraSound (TRUS) system may be used to perform a guided biopsy of the prostate in order to diagnose the malignancy of the tumor and its capacity to spread. TRUS images obtained with an ultrasound probe guide a physician inserting tiny radioactive seeds into the prostate during a transperinal brachytherapy. A perforated template is generally used to guide the physician during the insertion of the needle.

Unfortunately, TRUS offers limited contrast between tumors and healthy prostatic tissues, thereby inhibiting the identification of small tumors with diameter below 5 mm. This limits the efficiency of the biopsy, which is of great disadvantage. In fact, at least 20 percent of TRUS-guided prostate biopsy results in a false negative diagnosis, which implies that the cancer will go untreated, continue to evolve and spread if malignant.

Magnetic Resonance Imaging (MRI) systems may offer higher tumor perceptibility than standard TRUS procedures. However, MRI guidance implies to work in a specific environment. Indeed, typical clinical MRI systems generate magnetic fields ranging from 0.5 Tesla to 7 Tesla, hence no ferromagnetic objects can be introduced inside the MRI operating room since they would easily become dangerous projectiles. Moreover, MRI systems offer a very limited access to the patient, specially the closed-bore system.

Several MRI guided robots using MRI images have been proposed for breast, brain and prostate cancer treatments. For example, in the case of prostate treatment, a 6 Degree Of Freedom (DOF) robotic arm equipped with MRI compatible ultrasonic motors has been proposed for needle guidance procedures. However, they contain conducting materials creating Eddy currents which may interfere with the MRI magnetic field, thus generating image artifacts, which is of great disadvantage.

Pneumatic systems made with all-plastic components have also been proposed for offering optimal MRI compatibility. MRI compatible pneumatic step motors have been developed and integrated to a manipulator in order to move a 6 DOF robot. The proposed step motors use piezoelectric elements to control a compressed air flow, while the manipulator's position is measured by MRI compatible optical encoders. Many parts are involved in this complex design and step motors might skip steps and lose accuracy, which is of great disadvantage.

A different 6 DOF approach using linear pneumatic cylinders has also been proposed. In this system, the cylinders are actuated by pneumatic proportional pressure regulator valves controlled by piezoelectric elements. The pressure control system is located at the foot of the bed in order to limit non-linearity caused by air compressibility. To even reduce the non-linearity, special low friction cylinders may be used but it increases the cost of the system. Moreover, a complex control system should be used, which even increase the complexity and cost of the system.

It would therefore be desirable to provide an object manipulator that will reduce at least one of the above-mentioned drawbacks.

BRIEF SUMMARY

Accordingly, there is disclosed a device for orienting an object according to a given spatial orientation. The device comprises a frame and a supporting member adapted for supporting at least a portion of the object, the supporting member being operatively connected to the frame. The device for orienting an object comprises a plurality of fluid actuated devices for displacing the supporting member with respect to the frame, each of the fluid actuated devices having a first end connected to the frame and a second end connected to the supporting member. Each of the fluid actuated devices is actuatable between a first position wherein the device has a first length and a second position wherein the device has a second length. The device for orienting comprises an actuation mechanism comprising a plurality of actuating valves, each being respectively operatively connected to a corresponding fluid actuated device for actuating the corresponding fluid actuated device between the first position and the second position; wherein an actuation of at least one of the fluid actuated devices enables to displace the supporting member with respect to the frame, thereby orienting the object according to the given spatial orientation.

The device for orienting may be of particular interest as an object manipulator for attaining a given target with a suitable accuracy in a structure extending proximate the device for orienting, which is of great advantage.

The device for orienting an object may be manufactured at a cost lower than prior art devices for orienting an object while enabling a suitable accuracy, which is of great advantage.

Moreover, in one embodiment, the device for orienting is simple to operate and may produce suitable force level to reach the required stiffness, which is of great advantage for providing a suitable accuracy in the positioning of the object with respect to a neighboring structure.

In one embodiment, the device for orienting is Magnetic Resonance Imaging (MRI) compatible.

This is of great advantage since the device may be used in an MRI environment or any other environment requiring a ferromagnetic free device.

In one embodiment, the frame has a circular hollow shape, the supporting member being mounted inside the frame.

In one embodiment, the second length of each of the fluid actuated devices is longer than the first length thereof, while in an alternative embodiment the first length of each of the fluid actuated devices is longer than the second length thereof.

In one embodiment, each of the actuating valves comprises a Dielectric Elastomer Actuator (DEA), which is of great advantage for providing a ferromagnetic free device.

In another embodiment, each of the actuating valves comprises a piezo-electric actuator, which is of great advantage for providing a ferromagnetic free device.

In one embodiment, each of the actuating valves comprises a bistable valve.

In another embodiment, the actuation mechanism is pneumatically actuated.

In one embodiment, each of the fluid actuated devices is mounted on a given plane for displacing the supporting member on the plane.

In a further embodiment, the device for orienting an object further comprises an additional plurality of fluid actuated devices arranged on a second plane spaced-apart from the first plane.

In still a further embodiment, the supporting member is operatively mounted on the first plane, the device further comprises an additional supporting member mounted on the second plane for supporting at least another portion of the object.

In one embodiment, the plurality of fluid actuated devices comprises from 2 to 24 devices and the additional plurality of fluid actuated devices comprises from 2 to 24 devices.

In a further embodiment, the plurality of fluid actuated devices comprises 6 devices and the additional plurality of fluid actuated devices comprises 6 devices.

In yet a further embodiment, the plurality of fluid actuated devices are arranged on a plurality of planes spaced apart from each others.

In one embodiment, the frame, the supporting member, the plurality of fluid actuated devices and the actuation mechanism are made from non-electrically conducting materials, which is of great advantage for providing a MRI compatible device.

In a further embodiment, the frame, the supporting member, the plurality of fluid actuated devices and the actuation mechanism are made from polymer materials, which is of great advantage for providing a MRI compatible device.

In one embodiment, each of the fluid actuated devices comprises an upper rigid fixture, a lower rigid fixture and a deformable hollow membrane mounted therebetween.

In a further embodiment, each of the deformable hollow membranes comprises a hyper-elastic material.

In yet a further embodiment, the hyper-elastic material is selected from a group consisting of polyurethane rubber, silicon, acrylic and natural rubber.

In one embodiment, the hyper-elastic material comprises a low visco-elastic material.

In one embodiment, the first position is a deflated position of the deformable hollow membrane and the second position is an inflated position of the deformable hollow membrane.

In one embodiment, at least one of the fluid actuated devices has a given first initial length when in the first position and at least one of the remaining fluid actuated devices has a given second initial length longer than the first initial length when in the first position.

In a further embodiment, the device for orienting an object further comprises a control unit operatively connected to the actuation mechanism for controlling the actuation of each of the fluid actuated devices.

In still a further embodiment, the device for orienting an object further comprises a position sensor operatively connected to the control unit for sensing an actual position of at least one of the supporting member and a tip of the object, which is of great advantage for enabling an accurate positioning of the object.

In one embodiment, each of the fluid actuated devices comprises a bistable fluid actuated device.

In another embodiment, the actuation mechanism is adapted to actuate each of the fluid actuated devices continuously between the first position and the second position.

In one embodiment, the plurality of fluid actuated devices is operatively connected between the frame and the supporting member and is adapted to enable an elastically averaged positioning of the supporting member, which is of great advantage for providing a suitable accuracy in the positioning of the object.

In one embodiment, the object comprises a medical device.

In a further embodiment, the object is selected from a group consisting of a medical needle, a trocart and an electrode.

In another embodiment, the object comprises a medical device for insertion of a therapeutic agent into an anatomical structure, the therapeutic agent being selected from a group consisting of a radioactive material, a cryogenic agent and a chemotherapy agent.

According to another aspect, there is also disclosed the use of the device for orienting an object as previously described, for prostate cancer diagnosis.

According to another aspect, there is also disclosed the use of the device for orienting an object as previously described, for attaining a given target in an anatomical structure extending proximate the device for orienting an object.

BRIEF DESCRIPTION OF THE DRAWINGS

In order that the invention may be readily understood, embodiments of the invention are illustrated by way of example in the accompanying drawings.

FIG. 7 is a graph showing the net force of an air muscle according to its deformed length, according to one embodiment.

FIG. 8 is a graph showing the position of the needle tip of a device for orienting using linear actuated devices, according to one embodiment.

FIG. 9 shows an experimental setup used to evaluate various characteristics of a fluid actuated device, according to an embodiment.

FIG. 10 is a graph showing the material characterization of rubber material used in one embodiment.

FIG. 11 shows a fluid actuated device in an inflated position and in a deflated position, according to one embodiment.

FIG. 12 is a graph showing the force applied to move a middle collar of an air muscle of a device for orienting, according to one embodiment.

FIG. 13A to 13C are tables illustrating selected parameters of a device for orienting, according to one embodiment.

FIG. 18A and FIG. 18B are tables showing sensitivity of a fluid actuated device of a device for orienting, according to one embodiment.

Further details of the invention and its advantages will be apparent from the detailed description included below.

DETAILED DESCRIPTION

In the following description of the embodiments, references to the accompanying drawings are by way of illustration of examples by which the invention may be practiced. It will be understood that various other embodiments may be made and used without departing from the scope of the invention disclosed.

The invention concerns a device for orienting an object according to a given spatial orientation which may be used in a great variety of applications such as in various medical applications for non-limitative examples.

Throughout the description, the device for orienting an object will be described in the particular application of prostate cancer treatment but the skilled addressee should appreciate that the device may be used in many applications where medical tool orientation and placement is key for the success of the treatment, as it will become apparent below.

The skilled addressee will also appreciate that the device for orienting may also be used in a great variety of other applications wherein ferromagnetic compatibility is required or in a flammable environment, as it will also become apparent below.

Referring to FIG. 2A to FIG. 5, an embodiment of a device 10 for orienting an object 12 according to a given spatial orientation will now be described. This embodiment may be of great interest for orienting a medical object according to a given spatial orientation or direction, for example for reaching specific targets in an anatomical structure (not shown) with a suitable accuracy, as it will become apparent below.

The device 10 comprises a frame 14 and a supporting member 16 adapted for supporting at least a portion of the object 12. The supporting member 16 is operatively connected to the frame 14. In the illustrated embodiment, the frame 14 has a circular hollow shape and the supporting member 16 is mounted inside the frame 14, as explained below. Still in the illustrated embodiment, the object 12 comprises a medical needle. The skilled addressee will however appreciate that various other arrangements may be considered.

Figure 5:
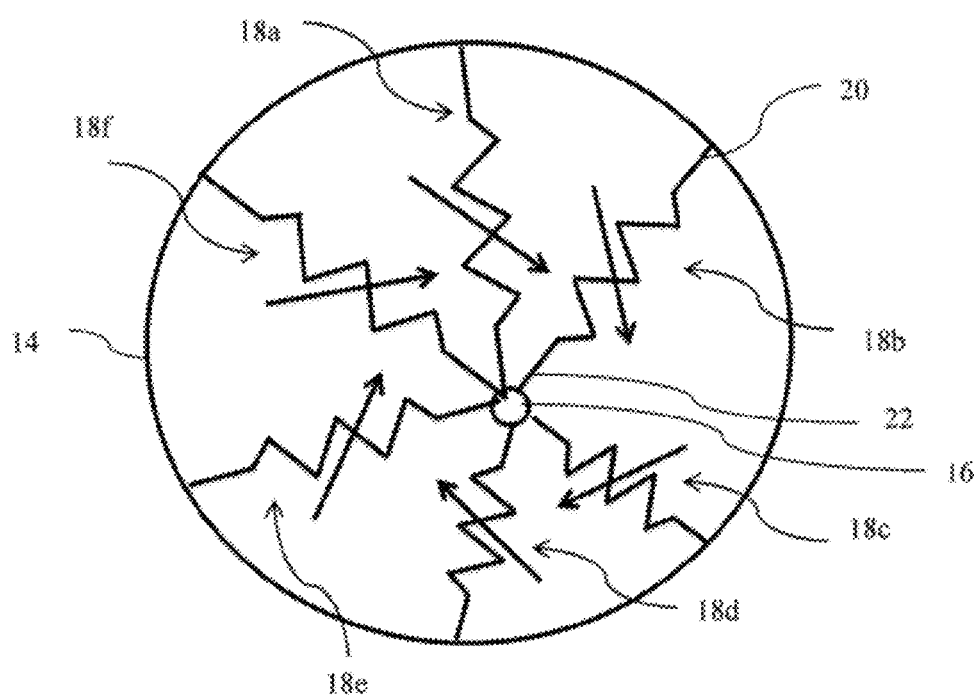
FIG. 5 is a schematics of a portion of a device for orienting an object according to a given spatial orientation, according to another embodiment.

As better shown in FIG. 5, the device 10 comprises a plurality of fluid actuated devices 18a, 18b, 18c, 18d, 18e, 18f for displacing the supporting member 16 with respect to the frame 14. Each of the fluid actuated devices 18a, 18b, 18c, 18d, 18e, 18f has a first end 20 connected to the frame 14 and a second end 22 connected to the supporting member 16.

As illustrated in FIG. 5, each of the fluid actuated devices 18a, 18b, 18c, 18d, 18e, 18f is actuatable between a first position wherein the device has a first length and a second position wherein the device has a second length. In the illustrated embodiment, some of the fluid actuated devices 18a, 18b, 18c, 18d, 18e, 18f extend in the first position while the others extends in the second position, as it will become apparent below.

Referring again to FIG. 2A, the device 10 for orienting also comprises an actuation mechanism comprising a plurality of actuating valves 24a, 24b, 24c, 24d, 24e, 24f, each being respectively operatively connected to a corresponding fluid actuated device 18a, 18b, 18c, 18d, 18e, 18f for actuating the corresponding fluid actuated device between the first position and the second position.

As shown in FIG. 5, an actuation of at least one of the fluid actuated devices 18a, 18b, 18c, 18d, 18e, 18f enables to displace the supporting member 16 with respect to the frame 14, thereby orienting the object 12 according to the given spatial orientation, as it will become apparent below.

The skilled addressee will appreciate that in the embodiments illustrated in FIGS. 2A and 5, the fluid actuated devices 18a to 18f are schematically illustrated as elastic springs but this schematic representation should not be understood as limited to the use of springs, as it will become apparent below.

Referring again to FIG. 2A, in a further embodiment, the device 10 for orienting an object 12 further comprises a control unit 26 operatively connected to the actuation mechanism for controlling the actuation of each of the fluid actuated devices 18a, 18b, 18c, 18d, 18e, 18f.

In one embodiment, the device 10 for orienting is operated according to a binary mode. In other words, each of the fluid actuated devices 18a, 18b, 18c, 18d, 18e, 18f comprises a bistable fluid actuated device which may only take two distinct states. Accordingly, each of the actuating valves 24a, 24b, 24c, 24d, 24e, 24f comprises a bistable valve. As it will become apparent below upon reading of the present description, such a binary operating mode may be of great advantage for a given application since the actuation and the control thereof may be greatly simplified.

In another embodiment, the actuation mechanism is adapted to actuate each of the fluid actuated devices 18a, 18b, 18c, 18d, 18e, 18f continuously between the first position and the second position. In other words, each of the fluid actuated devices 18a, 18b, 18c, 18d, 18e, 18f may take a plurality of positions between the first position and the second position. In this embodiment, the actuating valves 24a, 24b, 24c, 24d, 24e, 24f should be conveniently chosen to enable such a continuous operating mode.

In one embodiment, the control unit 26 may operate the device 10 for orienting an object 12 according to an open loop mode while in another embodiment a closed loop mode may be implemented, as better detailed thereinafter.

Referring again to FIG. 2A, in one embodiment, the device 10 for orienting an object 12 further comprises a position sensor 28 operatively connected to the control unit 26 for sensing an actual position of at least one of the supporting member 16 and a tip of the object 12.

Although the device 10 for orienting an object 12 may be operated according to an open loop mode, it may be of great advantage for a given application to operate the device according to a closed loop mode thanks to the position sensor 28, as apparent to the skilled addressee. In fact, the control unit 26 may monitor the actual position of the tip of the object 12 in order to correct for any calibration error or operating drift which may arise, as detailed below.

In one embodiment, the actuation mechanism is pneumatically actuated. In a further embodiment, the device 10 for orienting is operated with pressurized air. This is of great advantage when the device 10 for orienting an object 12 is used in an hospital or a similar environment since pressurized air is generally already available. The skilled addressee will nevertheless appreciate that other fluid may be used for operating the device 10, according to a given application.

In one embodiment, as illustrated in FIG. 5, each of the fluid actuated devices 18a, 18b, 18c, 18d, 18e, 18f is mounted on a given plane for displacing the supporting member 16 on the plane.

Figure 4:
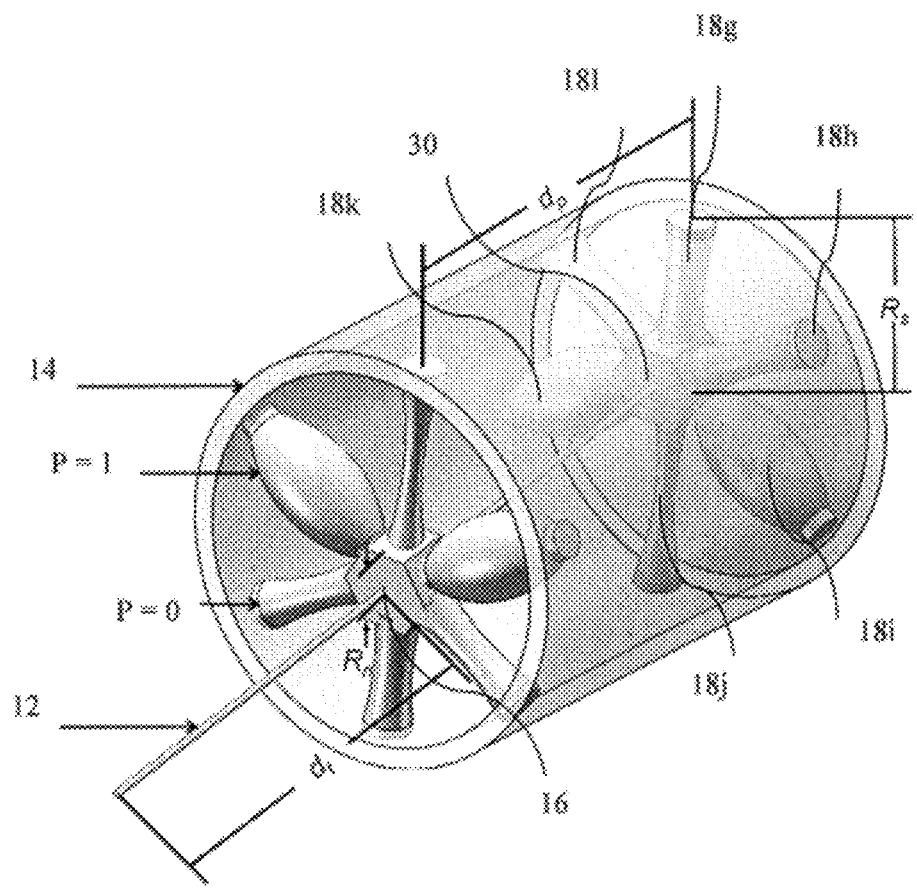
FIG. 4 is a perspective view of a portion of a device for orienting an object according to a given spatial orientation, according to another embodiment.

In a further embodiment, as illustrated in FIG. 4, the device 10 for orienting an object 12 further comprises an additional plurality of fluid actuated devices 18g, 18h, 18i, 18j, 18k, 18l arranged on a second plane spaced-apart from the first plane. In the illustrated embodiment, the supporting member 16 is operatively mounted on the first plane. The device 10 for orienting further comprises an additional supporting member 30 mounted on the second plane for supporting at least another portion of the object 12. In this embodiment, an additional plurality of actuating valves (not shown) is used for actuating the fluid actuated devices 18g, 18h, 18i, 18j, 18k, 18l.

The skilled addressee will appreciate that a single plane may be used. However, in one embodiment, two planes may be preferred since it enables a more accurate positioning of the object 12, for example a medical needle, as it will become apparent below. The skilled addressee will also appreciate that a plurality of planes may be considered for improving the accuracy of the positioning of the object. In one embodiment, the planes extend parallel to each other but other arrangements may be considered.

In the illustrated embodiment, the supporting member 16 is held in position with respect to the frame 14 via the fluid actuated devices 18a, 18b, 18c, 18d, 18e, 18f but it should be mentioned that other arrangements may be considered.

In the embodiment illustrated in FIG. 4, the plurality of fluid actuated devices comprises 6 devices 18a, 18b, 18c, 18d, 18e, 18f and the additional plurality of fluid actuated devices comprises 6 devices 18g, 18h, 18i, 18j, 18k, 18l, but the skilled addressee will appreciate that various other configurations may be envisaged. For example, in further embodiments, the plurality of fluid actuated devices may comprise from 2 to 24 devices and the additional plurality of fluid actuated devices may comprise from 2 to 24 devices.

The embodiments shown in FIG. 4 and in FIG. 5 are of great advantage since the dynamic mounting of the fluid actuated devices 18a, 18b, 18c, 18d, 18e, 18f between the frame 14 and the supporting member 16 enables an elastically averaged positioning of the supporting member, as it will be better detailed thereinafter.

Figure 2B:
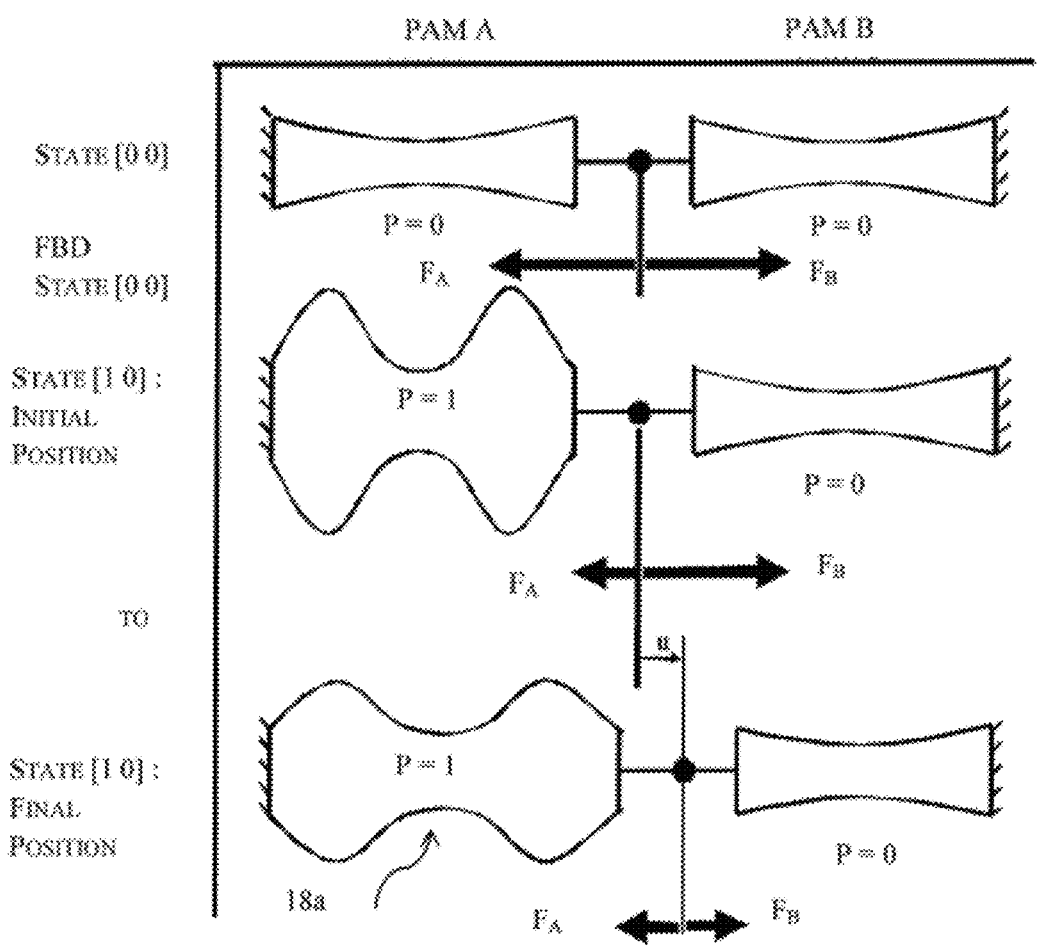
FIG. 2B illustrates the elastically average fluid actuated device principle.
Figure 2A:
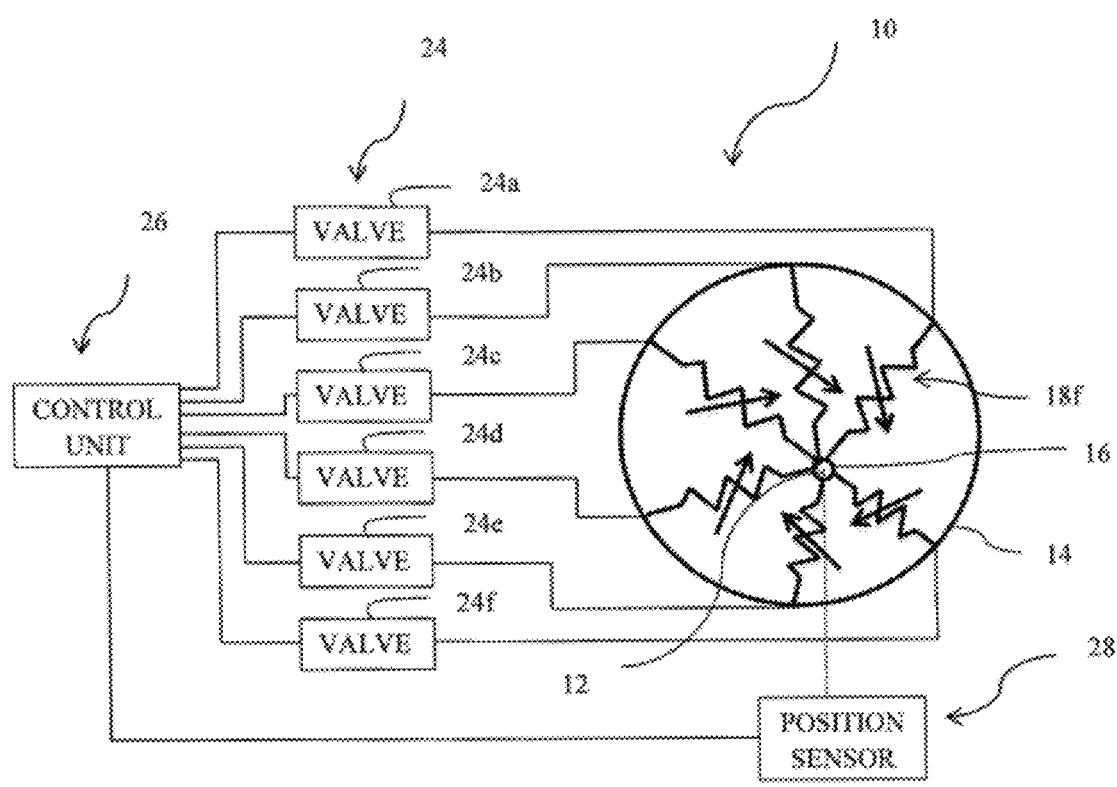
FIG. 2A is a schematics of an embodiment of a device for orienting an object according to a given spatial orientation.

FIG. 2B shows the basic operating principle of an elastically averaged binary fluid actuated device 18a in a single degree of freedom (u) system. Forces applied on the end effector (FA and FB) by the fluid actuated devices, along with the actuation pressure (P) states are presented by Free-Body Diagrams (FBD).

Figures 6A, 6B:
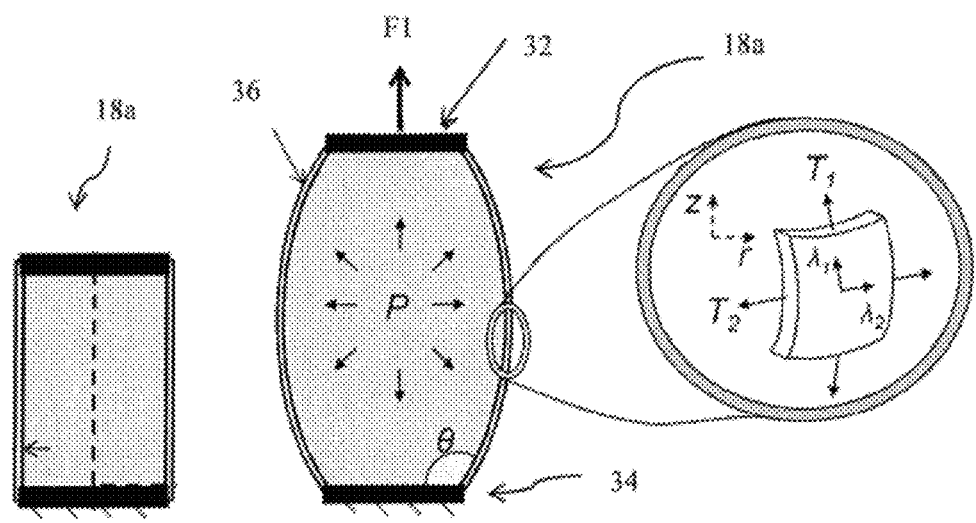
FIG. 6A and FIG. 6B show an embodiment of a fluid actuated device in a first deflated position and in a second inflated position respectively.

Referring now to FIG. 6A and FIG. 6B, an embodiment of a fluid actuated device 18a will now be described. In this embodiment, the fluid actuated device 18a comprises an upper rigid fixture 32, a lower rigid fixture 34 and a deformable hollow membrane 36 mounted therebetween. FIG. 6A shows the fluid actuated device 18a in the first position, which is a deflated position, while FIG. 6B shows the fluid actuated device 18a in the second position, which is an inflated position. In this embodiment, the fluid actuated device 18a has a first length when extending in the first position and a second length longer than the first length when extending in the second position, as illustrated in FIGS. 6A, 6B and 2B. As illustrated, in this embodiment, when the fluid actuated device 18a is actuated, fluid is forced inside the membrane 36 which deformed under the pressure of the fluid. The membrane 36 deforms axially but also longitudinally. Since one of the upper and lower fixtures 32, 34 is fixedly mounted with the frame 14, this longitudinal deformation pushes on the other fixture connected to the supporting member 16, thereby moving the supporting member 16 accordingly. As shown, in this embodiment, when actuated, the fluid actuated device 18a has a length longer than its initial length.

In one embodiment, each of the deformable hollow membranes 36 comprises a hyper-elastic material. In yet a further embodiment, the hyper-elastic material is selected from a group consisting of polyurethane rubber, silicon, acrylic and natural rubber. The skilled addressee will appreciate that a combination of these materials may be used. The skilled addressee will also appreciate that other materials having a suitable elasticity and enabling a temporary deformation under the pressure of a fluid may be considered.

In one embodiment, the hyper-elastic material comprises a low visco-elastic material.

In the embodiment illustrated in FIG. 4, each of the fluid actuated devices 18a, 18b, 18c, 18d, 18e, 18f has the same initial length. However, in another embodiment, at least one of the fluid actuated devices 18a, 18b, 18c, 18d, 18e, 18f may have a given first initial length while the remaining fluid actuated devices may have a given second initial length longer than the first initial length when extending in the first position. This may be of great advantage for enabling a uniform distribution of the possible positions of the tip of the needle in a given workspace, as further described below.

In the embodiments described above, the fluid actuated devices 18a to 18f have been described as having an expanded length when actuated. The skilled addressee will nevertheless appreciate that other arrangements may be considered. For example, in an alternative embodiment, the fluid actuated devices may have a contracted length when actuated, as well described in "Pneumatic Actuating Systems for Automatic Equipment", Igor L. Krivts, 2006.

Figure 3:
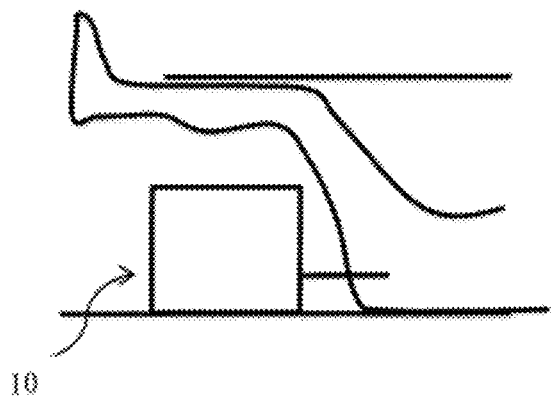
FIG. 3 is a schematics of another embodiment of a device for orienting an object according to a given spatial orientation, the device being used in a MRI system.

Referring now to FIG. 3, as mentioned above, the device 10 for orienting an object 12 as previously described may be of great interest in the medical sector for robot-guided interventions for example.

In one embodiment, the device 10 for orienting an object 12 is used in a MRI environment, i.e. the device 10 is used proximate a magnet (not shown) so the device is adapted to be Magnetic Resonance Imaging (MRI) compatible.

Accordingly, in one embodiment, the frame 14, the supporting member 16, the plurality of fluid actuated devices 18a, 18b, 18c, 18d, 18e, 18f and the actuation mechanism are made from non-electrically conducting materials. In a further embodiment, the frame 14, the supporting member 16, the plurality of fluid actuated devices 18a, 18b, 18c, 18d, 18e, 18f and the actuation mechanism are made from polymer materials. In another embodiment, the frame 14 may be made of plastic of fiber glass.

In one embodiment, each of the actuating valves 24a, 24b, 24c, 24d, 24e, 24f comprises a Dielectric Elastomer Actuator (DEA). In another embodiment, each of the actuating valves 24a, 24b, 24c, 24d, 24e, 24f comprises a piezo-electric actuator. The skilled addressee will however appreciate that other arrangements may be considered for providing a MRI compatible device.

As mentioned above, although the device 10 for orienting as previously described may be useful in a great variety of application, one application is in the medical sector for manipulating and orienting a medical device in order to reach a given target in an anatomical structure with a suitable accuracy.

Indeed, in one embodiment, the object 12 comprises a medical needle for insertion into an anatomical structure such as a prostate for a non-limitative example and as detailed below. In another embodiment, the object 12 may comprise a trocart or an electrode or any other medical device which has to be particularly positioned with respect to the anatomical structure before interacting therewith. For example, the medical device may be used to perform a biopsy, as known to the skilled addressee. It may also be used for insertion of a therapeutic agent into an anatomical structure, the therapeutic agent being selected from a group consisting of a radioactive material, a cryogenic agent and a chemotherapy agent, as well known in the art to which the invention pertains.

Referring again to FIG. 3, the device 10 for orienting an object 12 as previously described may be of particular interest for improving current medical procedures. Indeed, the device 10 for orienting may be used as a needle manipulator to precisely reach small tumours whose diameter is less than 5 mm inside the anatomical structure such as the prostate. Such an embodiment will be described below.

Since, in this embodiment, the needle manipulator is to be used in a MRI environment, it is designed to be MRI compatible, i.e. ferromagnetic free, as described above.

Moreover, the needle manipulator is designed to be compact enough in order to be usable inside a closed-bore MRI system wherein the available space is more limited than in an open-bore MRI system, which is of great advantage. In one embodiment, the needle manipulator is designed to have an overall shape of about 200 mm×200 mm×200 mm, as illustrated in FIG. 3.

In the embodiment illustrated in FIG. 3, the selected approach is the transperinal in the lithotomic position. The manipulator is placed between the patient's legs in order to scan the prostate.

In the case of prostate cancer treatment, the needle manipulator should allow a positioning of the needle in a three dimensional workspace of 70 mm in width, 80 mm in height and 70 mm in depth, in order to cover a complete cancerous prostate located at 60 mm away from the perineum.

As detailed below, the needle manipulator is adapted to offer a suitable accuracy in the positioning and orientation of the needle in order to precisely reach a small tumor whose diameter is less than 5 mm.

As previously mentioned, the primary requirement of an intra-MRI needle manipulator is that it has to be MRI compatible. Ferromagnetic actuator cannot be used inside magnetic fields, considerably reducing the choice of actuators available for the robot's design. Electrical energy should also be shutdown during the imaging process, in order to preserve the integrity of the magnetic field produced by the MRI and therefore to avoid image artifacts. The system components should also preferably be made from polymer materials in order to avoid Eddy currents that can interfere with the MRI signal, as described above.

Brachytherapy techniques of the prior art using a template with holes at every 5 mm, offer an accuracy of about 2 mm. Here, accuracy is defined as the minimal distance between any random point in space (bound to the workspace) and the actual closest point that the system may achieve. The needle manipulator accuracy is therefore set to 1 mm in order to improve from prior art techniques.

To maintain the needle in its desired position during insertion, the manipulator should hold 1.6 N in the radial direction and 15 N in the axial direction. In order to prevent excessive deflection of the needle under load, the required system radial stiffness at the needle tip must be at least 0.32 N/mm. This enables a suitable perforation of the skin, as known to the skilled addressee. With such stiffness, the needle will not deviate more than 5 mm, therefore improving over the manipulator's precision of the prior art.

As described above, referring again to FIG. 4 and FIG. 5, when actuated, the fluid actuated devices 18a to 18f, also referred to as the air muscles hereinafter, which are made from hyperelastic polymer such as polyurethane rubber or silicon in one embodiment, are deformed by the pneumatic energy. In this embodiment, these particular muscles do not comprise specifically oriented fibers such as McKibben muscles, although the latter may be considered.

Figure 1:
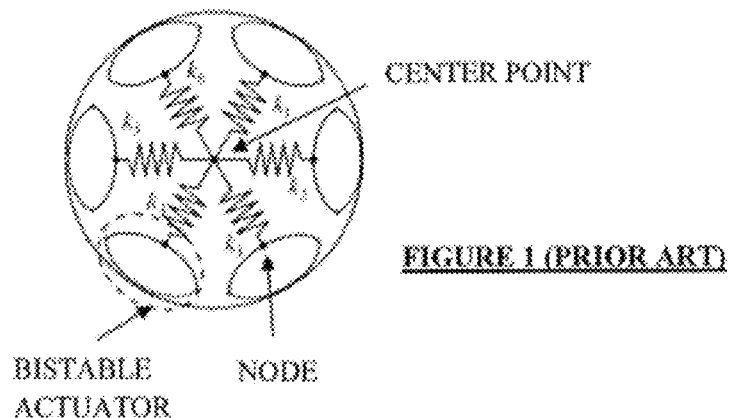
FIG. 1 (PRIOR ART) shows an object manipulator of the prior art.

The air muscles described below are designed to have a compact volume while producing high volumetric force, which can help reducing the overall system volume while obtaining satisfactory system stiffness. This is of great advantage for providing a system usable in a MRI environment wherein the available space is reduced. Indeed, as mentioned above, it enables to provide a needle manipulator having an overall shape fitting in the available volume, which is of great advantage compared to the manipulator previously proposed by Plante, J. and Dubowsky, S. in "Advances in Robot Kinematics: Analysis and Design", 2008, Springer, Netherlands, pp. 391-398, and illustrated in FIG. 1. Indeed, this prior art system has a diameter of about 550 mm and is therefore not usable in a closed bore MRI system.

The air muscles inherent compliance also accommodates the different actuator's states, thereby reducing the robot's complexity and volume compared to a complex spring assembly, as it will become apparent below.

In this embodiment, the muscles are bistable, i.e. they have two states, namely an inflated position when pressure is applied and a deflated position when no pressure is applied thereto. Binary control is provided by on/off spool valves that enable the manipulator to maintain a stable position without continuous electrical energy being supplied to the valves, which is of great advantage since it reduces the risk of interferences with the MRI signal. These valves are driven by MRI compatible actuators such as piezoelectric or DEA actuators, as mentioned above. When inflated, the air muscles are held at constant pressure to avoid needle drift which may be caused by air pressure fluctuations, such as an air leakage. In this embodiment, air compressibility does not influence the system's compliance as the elastic membranes are chosen to be significantly stiffer than the air volume acting upon them.

The schematic of one plane of the needle manipulator is illustrated in FIG. 5. In one embodiment, 12 anchor points distributed on 2 planes considered as spherical pivots are used for connecting the air muscles between the frame and the supporting element supporting the needle. The supporting element is connected to the frame through each of the air muscles.

In this embodiment, as it will become apparent below to the skilled addressee, the air muscles are assumed to be active non-linear springs which have different force/deformed length profiles determined by their geometry and inflation pressure. In the illustrated embodiment, the various needle equilibrium positions are defined by the different binary actuation states of the overconstrained system. Still in this embodiment, the air muscles are pre-stretched and designed to remain in tension for all actuation states.

Still referring to FIG. 5, for any given actuation states, the analytical model evaluates the needle position that minimizes the system's potential conservative energy, expressed by:

$$U = U_g + W_{ext} + U_E \tag{1}$$

$$U = m_{needle}gh + F_{ext}\delta + \sum_{i=1}^{nairmuscles} \int_0^\zeta F_{airmuscle} d\zeta \tag{2}$$

$$\zeta = L_{spring\ i} - L_{0i} \tag{3}$$

where Lspring i is the deformed length of the air muscle, L0 i is the length at zero force (free length) and ζ is the elongation. The muscle's free length depends on actuation pressure, as described below with reference to FIG. 7. The global potential energy equation (U) includes the gravitational energy (Ug) associated to an elevation (h) of the needle's center of mass, the conservative work (Wext) applied on the needle by external forces (Fext) and the conservative elastic energy (UE) associated to the n air muscles where each muscle has its own force/deformed length (Fair muscle) characteristic.

In this positioning model, each air muscle's length is determined with a full 3D representation of the systems kinematics without the use of any geometrical approximation. As shown in FIG. 5, a needle coordinate system (x',y') is fixed on the needle tip and describes the needle anchor points (Ani), the center of mass position and the perturbation load applied on the needle. A fixed frame coordinate system (x, y) is used to express all frame related anchor points (Afi). The needle coordinate system is therefore mobile and the frame coordinate system is fixed. Euler angles (ROT) and translational (TRANS) matrices link the two coordinate systems and are used to calculate the spring length of each air muscle in the frame's coordinate system by:

$$L_{springi} = |A_{fi} - (A_{ni}\text{ROT} + \text{TRANS})| \tag{4}$$

For each given set of input pressures, the transformation matrices (ROT and TRANS) are found iteratively, until the global energy expressed by Equation 2 is minimized by the Nelder-Mead's method (MATLAB®), as known to the skilled addressee. Those two transformation matrices can then be used to locate the needle tip in the frame coordinate system for a given actuation state.

Referring now to FIGS. 6A and 6B, an air muscle model will now be described, according to one embodiment.

To determine the axial force developed by the air muscles, a continuum mechanics approach was used to model the axisymmetric membrane. A detailed development of such membranes is explained in Yang & Feng, 1970, "On Asymmetrical Deformations of Nonlinear Membranes", Transactions of the ASME, Series E, Journal of Applied Mechanics, 37(4) pp. 1002-11.

FIG. 6A and FIG. 6B show a schematic of an air muscle along with its key geometric variables, according to one embodiment. In FIG. 6A, H represents the initial length of the muscle, when no pressure or force is applied on the muscle. The air muscles material is assumed to be hyperelastic and incompressible. A Mooney-Rivlin free energy function (W) describes the hyperelastic behavior in terms of the principal invariants I1 and I2:

$$W(I_1, I_2) = C_1(I_1 - 3) + C_2(I_2 - 3) \tag{5}$$

$$\alpha = \frac{C_2}{C_1} \tag{6}$$

$$I_1 = \lambda_1^2 + \lambda_2^2 + \lambda_3^2 \tag{7}$$

$$I_2 = \lambda_1^2\lambda_2^2 + \lambda_2^2\lambda_3^2 + \lambda_3^2\lambda_1^2 \tag{8}$$

$$\lambda_3 = \frac{1}{\lambda_1\lambda_2} \tag{9}$$

where C1 and C2 are material constants, I1 and I2 are principal invariants of the deformation tensor and λi are the principal stretch ratios. FIG. 6B shows the principal directions, the geometrical parameters and the coordinate system of one air muscle. The principal stretches of the membrane are determined by solving the following differential equation system:

$$\dot{\lambda}_1 = \frac{\lambda_2}{\left(\frac{1}{\lambda_2} + \frac{3}{\lambda_1^4\lambda_2^3}\right)(1+\alpha\lambda_2^2)} \times \left\{ \begin{array}{l} \frac{1}{\lambda_2}\left[\frac{\lambda_2}{\lambda_1} - \frac{\lambda_1}{\lambda_2} - \alpha\left(\frac{1}{\lambda_1\lambda_2^3} - \frac{1}{\lambda_1^3\lambda_2}\right)\right] - \\ \left(\frac{3}{\lambda_1^3\lambda_2^4} - \frac{\lambda_1}{\lambda_2^2}\right)\times(1+\alpha\lambda_2^2) - \left(\frac{\lambda_1}{\lambda_2} - \frac{1}{\lambda_1^3\lambda_2}\right)2\alpha\lambda_2^2 \end{array} \right\} \tag{10}$$

$$\dot{\lambda}_2 = \frac{\lambda_2\dot{\lambda}_1}{\lambda_1} + \frac{(\lambda_1^2 - \lambda_2^2)\left(\frac{\lambda_2}{\lambda_1} - \frac{1}{\lambda_1^3\lambda_2^3}\right)(1+\alpha\lambda_1^2)}{\lambda_2\left(\frac{\lambda_2}{\lambda_1} - \frac{1}{\lambda_1^3\lambda_2^3}\right)(1+\alpha\lambda_2^2)} - \frac{P(\lambda_1^2 - \lambda_2^2)^{1/2}\lambda_1 r_0}{2C_1h\left(\frac{\lambda_2}{\lambda_1} - \frac{1}{\lambda_1^3\lambda_2^3}\right)(1+\alpha\lambda_2^2)} \tag{11}$$

where dot means differentiation by z/r0. This system may be solved by imposing the following boundary conditions:

λ₂=1 at z/r₀=0

λ₁=λ₀ at z/r₀=0

$$\lambda_2 = 0 \text{ at } z/r_0 = H/(2r_0) \tag{12}$$

where λ0 is the initial stretch in the membrane at z=0. When solved for various λ0, the force deployed by the air muscle is function of its deformed length and is evaluated by:

$$\sin(\theta) = \frac{(\lambda_1^2 - \lambda_2^2)^{1/2}}{\lambda_1}\bigg|_{z=0} \tag{13}$$

$$F_1 = 4\pi\sin(\theta)C_1hr_0\lambda_2\left(\frac{\lambda_1}{\lambda_2} - \frac{1}{\lambda_1^3\lambda_2^3}\right)(1+\alpha\lambda_2^2)\bigg|_{z=0}$$

The skilled addressee will appreciate that this function is valid only for a muscle under mechanical tension because when under compression, the membrane is subject to buckling. Moreover, it has been shown that the Mooney-Rivlin model is more reliable for uniaxial stretches under 3. Those two boundaries are used to define the range of displacement available for the needle positioning.

With reference to FIG. 7, a Finite Element Analysis (FEA) will now be detailed.

FIG. 7 shows that the analytically predicted force response using Eq. 13 matches FEA (ANSYS®) results. This validation shows that the air muscle model is reliable and may be used with confidence in the positioning model. FIG. 7 also shows that the muscle's free length is increased when pressure is applied to it.

In one embodiment, to reduce computation time, the force/deformed length profiles of the air muscles are introduced in the positioning model as fifth order polynomial functions. The skilled addressee will nevertheless appreciate that various other arrangements may be considered for a given application.

Non-linear springs with decreasing stiffness may show horizontal portions in their force/deformed length curves causing local minima in the global potential energy function described above. Also, these horizontal portions have no stiffness generating excessively large displacements when subject to even the smallest perturbations. Hence, the air muscles have been designed to avoid these potential issues by verifying that force/deformed length characteristic curve avoids local minima and thus low stiffness.

In order to experimentally validate the positioning model, a 12 DOF manipulator prototype equipped with linear spring is built. Linear springs are chosen to simplify the validation of the needle positioning algorithm for a full 12 DOF system.

The prototype comprises a 290 mm diameter cylinder in which two planes of six studs are positioned through aligned holes. These holes are equally spaced 60 degrees apart while the two planes are offset by 180 mm. The needle tip is located 12.5 mm away from the first plane. To simulate actuation and modify the position of the needle, the studs are moved manually between the two binary positions spaced 13 mm apart.

Eight tests were performed using randomly chosen actuation states. The position of the needle tip was then measured and compared to the position predicted by the model. FIG. 8 shows the predicted position of the tip of the needle versus the detected experimental position. Measurements were achieved by probing the needle tip using a digital milling machine tool with a ±0.015 mm accuracy. In this experimentation, the measured average accuracy error was 0.6 mm. During contact, a slight displacement of the needle tip may have occurred which could explain some experimental errors. Nevertheless, the results show that the positioning model is accurate enough for design purposes.

Referring now to FIG. 11, a one DOF prototype was built to experimentally validate the elastic positioning model using air muscles as actuators and as a non linear compliant structure. This set-up is designed to estimate the system's displacement as well as its stiffness, depending on a given actuation state. A tensile testing machine (TA-XT Plus Texture Analyzer) is used to acquire the experimental force/displacement curve. As illustrated, to probe the supporting middle collar, only the lower air muscle is inflated at a constant pressure. In the experiment, the air muscles are made of rubber tubes on which the Mooney-Rivlin model is fitted.

Referring now to FIG. 12, material characterization of the 1 DOF prototype will now be described.

The material constants $C_1$ and $C_2$ used in the air-muscle model were determined experimentally from a tensile test. To find the material constants, the error between the model prediction (F1 in FIG. 6B) and the experiment is minimized by an iterative process. FIG. 10 shows the resulting analytical curve using the selected constants. The material constants defined in the analysis were found for a deformed length of about 160% of the tube, which is enough to accurately simulate the behavior of the air muscles in this experiment. FIG. 10 also demonstrates that the polymer membrane used in this simulation presents a significant viscoelastic behavior. No viscoelastic model was used in this experiment because the air muscles may be made out of a low viscoelastic material such as silicon, which would only improve model and experimental agreement. Nevertheless, the material model was approximately fit between the curves obtained from the traction test at 0.1 mm/s. This was done to average out opposite muscle behaviors of the 1 DOF prototype, one muscle being extended by actuation while it's conjugate is released.

Using the set-up shown in FIG. 9, stiffness measurements are done at a speed of 0.1 mm/s in order to match the evaluated material constants and to limit the influence of the viscoelastic effect. For accurate measurements when actuation is achieved, the position is probed when the middle collar is stabilized. This is found by verifying that the force applied on the probe is stable at 0 N.

With reference to FIG. 11, the actuation displacement obtained from the 1 DOF prototype will now be described.

Using the texture analyzer mentioned above, it was possible to determine the displacement of the center position. FIG. 11 shows 3.1 mm of displacement when the lower air muscle is inflated to 90 kPa.

For parameters presented on FIG. 11, a 3.9 mm displacement was estimated by the air muscle positioning model, indicating a 0.8 mm difference between the model and the experiment. Even if there is some error, the model accuracy is sufficient for design purposes. The positioning model for hyperelastic air muscles can therefore be used in the prediction of a complete workspace of a 12 DOF manipulator. The error can be explained by the viscoelastic nature of the air muscle material available for the experiment which may deviate the results according to actuation history.

Referring to FIG. 12, the prototype stiffness will now be discussed.

The stiffness of the 1 DOF prototype was measured by recording the force response of the experimental setup when moving 5 mm away from the equilibrium position. The average stiffness of the setup was linearly approximated between 2 to 4 mm. FIG. 12 shows the analytical and the experimental force response used in the stiffness evaluation. As illustrated, the analytical force response curves match accurately the experiments.

When no pressure is applied to either air muscles, the average predicted stiffness is 7.7 N/mm. Experiment shows a stiffness of 8.6 N/mm, indicating a difference of 10%. In the case where the lower muscle is pressurized, the predicted stiffness is of 10.0 N/mm while the experiment shows 9.9 N/mm, and thus a 0.1% error. The relatively low error shows that the analytical model is able to accurately predict the stiffness behavior of the 1 DOF prototype.

FIG. 13A to 13C show the manipulator's design parameters selected to meet chosen clinical requirements, according to one embodiment. This configuration may then be used to verify the manipulator's capacity to meet its design requirements such as workspace, accuracy, stiffness and volume discussed above.

Figure 14:
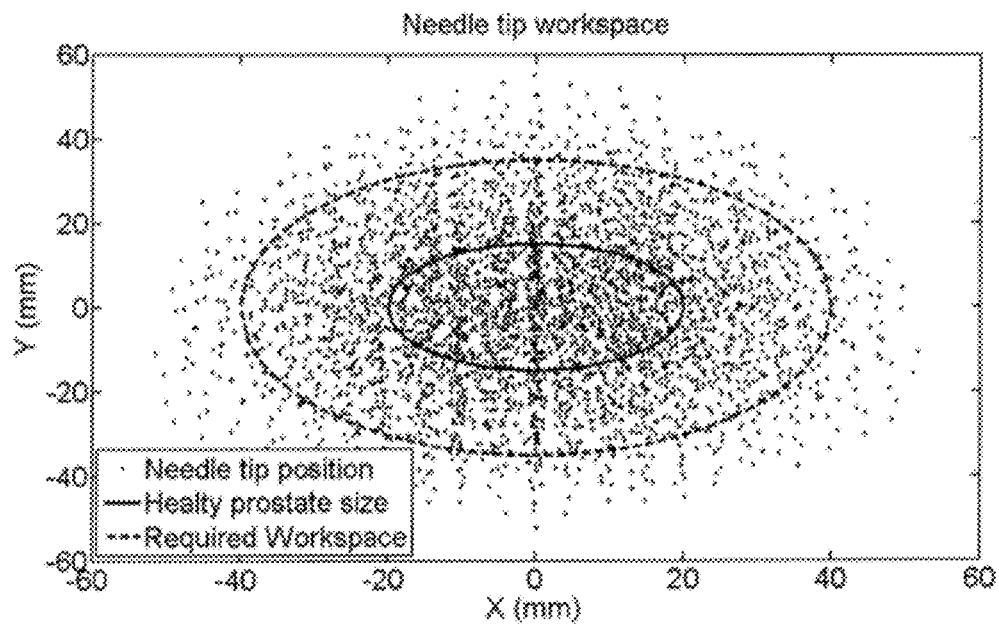
FIG. 14 is a graph illustrating each possible position for the tip of a needle spatially oriented with a device for orienting an object, according to one embodiment.

FIG. 14 shows all 4096 (212) available discrete positions that the needle tip can occupy at 35 mm depth into the prostate when using a device for orienting comprising 12 air muscles. As known to the skilled addressee, binary systems may only reach a finite set of points and these points should be evenly distributed in the required workspace. Thus, it may be of great advantage to break all system symmetries. To do so, in one embodiment the air muscle assemblies of each planes therefore have varying initial lengths, as described above and shown in FIG. 13B.

Figure 15:
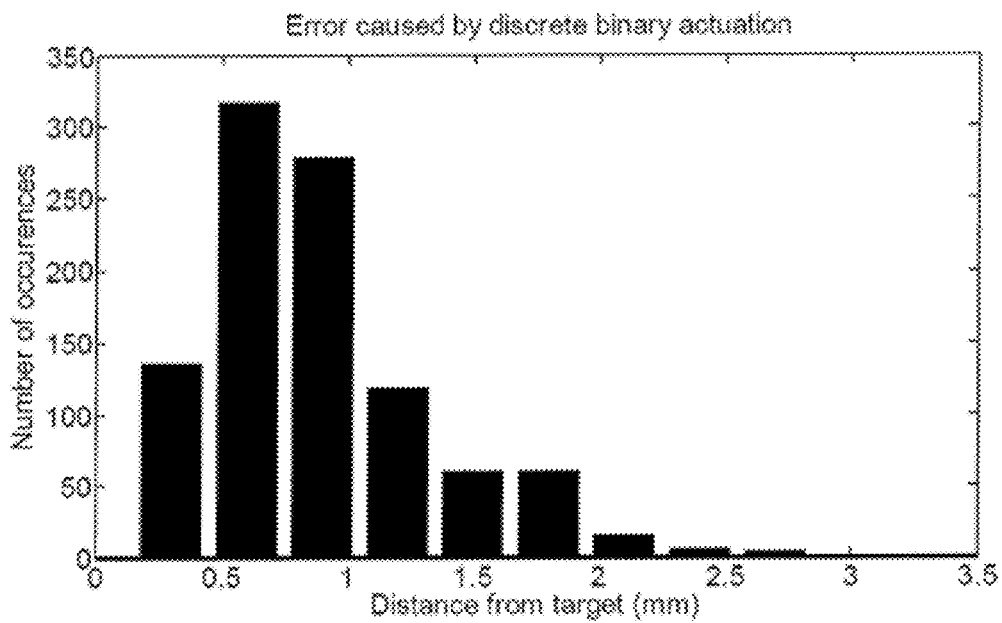
FIG. 15 is a graph showing an error distribution caused by a discrete binary actuation, according to one embodiment.

FIG. 15 shows the absolute error for 1000 randomly chosen targets in the required workspace. The distribution average is 0.7 mm and the median is 0.6 mm with a standard deviation of 0.48 mm. These results are suitable over the results of other prior art MRI compatible manipulators.

Figure 16:
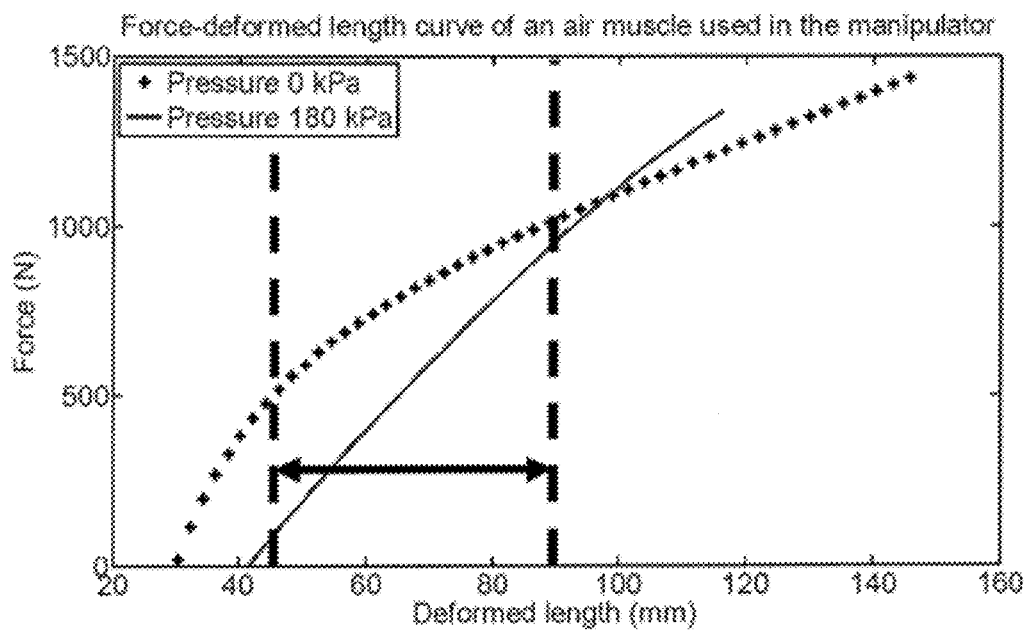
FIG. 16 is a graph showing the deformed length of a fluid actuated device according to the force applied thereon, according to one embodiment.

FIG. 16 presents the force/deformed length curve, starting at free-length, of a typical air muscle used in the proposed design. Clearly, the air muscle can provide substantial forces that can lead to high system rigidity. Rigidity as well as free length of the air muscle both change with the pressure application. When pressure is applied, the muscle's free length increases and stiffness decreases. The skilled addressee will note that the used positioning model is designed to limit the air muscle between its free length and three times its initial length although other arrangements may be considered.

Figure 17:
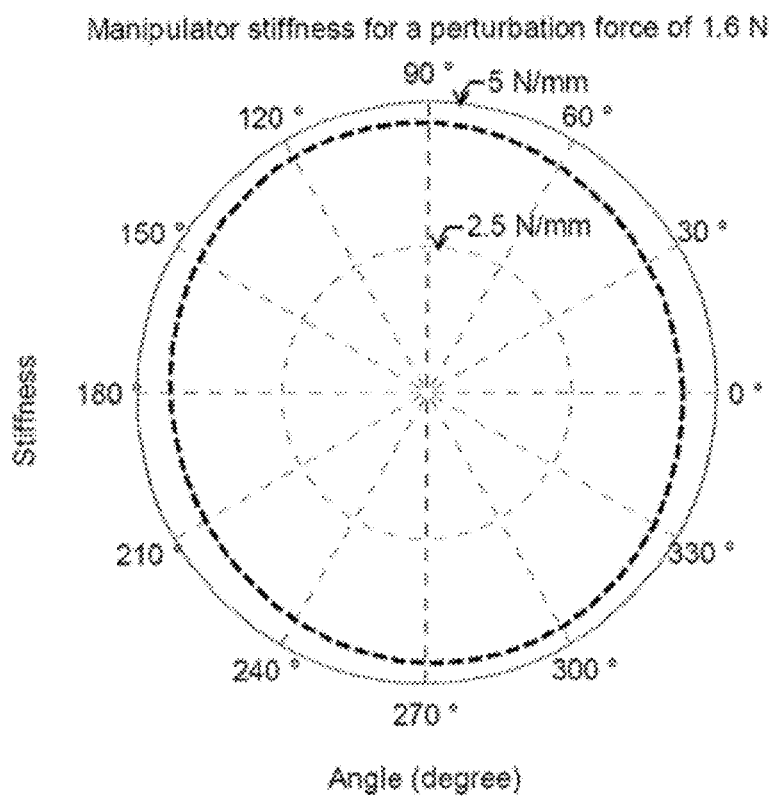
FIG. 17 is a schematics showing the stiffness at each angle of a device for orienting an object according to a given spatial orientation, according to one embodiment.

The overall system's stiffness is obtained by calculating the resulting displacement of the needle tip when a radial force of 1.6 N is applied at any angle around the needle. FIG. 17 shows a radial plot of the stiffness pattern of the proposed needle manipulator. An equivalent stiffness of about 4.5 N/mm is found all around the needle tip when all muscles are in an actuated state. The corresponding deviation from a needle insertion force of 1.6 N is 0.35 mm. The system's stiffness is found sufficient to fulfill clinical requirements.

A sensitivity analysis is performed to evaluate the impact of key design parameters variations. Initial length, material constants, pressure, wall thickness and initial radius are explored.

In order to study the sensitivity of the positioning model, a normally distributed error was added to some nominal parameters described in FIG. 13A to 13C. This error was computed by using a random noise covering 30% of the nominal value on six standard deviations. The predicted position of the needle tip was then calculated over the 4096 positions and compared to the positions obtained with nominal parameters to estimate a positioning error at needle tip. FIG. 18A indicates the average positioning error obtained by this simulation depending on which parameter the error was applied on.

The analysis shows that the air muscle manufacturing process is critical in achieving the needed accuracy. Moreover, the pressure regulation should also be controlled accurately. This however, may be easily controlled to ±1% error due to current pressure regulator technology available for the experiment.

The air muscle manipulator concept sensitivity is compared to the one of a manipulator system using linear springs and bistable DEAs. FIGS. 18A and 18B show that the geometrical parameters of both systems have similar impact on the positioning error. Preliminary studies have shown that calibrating elastically averaged binary manipulators may reduce prediction errors by up to an order of magnitude.

The feasibility of a needle manipulator concept using binary air muscle actuators has been evaluated as an acute and cost-effective intra MRI prostate cancer treatment tool. To determine the proposed manipulator's workspace, stiffness, volume, accuracy and sensitivity, a needle positioning model was developed. The model shows good agreement with experimental results obtained with a 12 DOF manipulator using linear springs and a 1 DOF prototype using air muscles.

The positioning model was used to size a manipulator that satisfies the chosen clinical requirements. The manipulator size is small enough to fit between the patient's legs when in a lithotomic position in a closed bore MRI system. The generated needle tip workspace is large enough to cover the entire cancerous prostate area. Also, the stiffness of the manipulator (4.5 N/mm) is found sufficient to sustain the radial penetration loads (1.6 N) applied on the needle. The manipulator's accuracy is 0.7 mm, which is similar to what other prostatic MRI compatible manipulators offer. Finally, a sensitivity analysis was performed on various parameters, showing that accurate pressure regulation as well as accurate manufacturing is needed to achieve an accurate manipulator.

Nonetheless, a calibration algorithm may be applied to the model, which would enhance the manipulator's accuracy.

The skilled addressee will appreciate that the device for orienting an object as previously described may constitute an active compliant mechanism where the compliance relieves the over-constraint imposed by the redundant parallel architecture.

Although a specific embodiment has been described, the skilled addressee will nevertheless appreciate that various other configurations may be envisaged for a given application, in the medical sector or in any other field wherein an accurate positioning of an object is required.

For example, the device may be used in a MRI environment as well as in a computed tomography environment or other various imaging environments. As non limitative examples, the device may be used for biopsy or brachytherapy treatments.

Moreover, even if well adapted for prostate treatment, it may also be used for the treatment of kidney, liver, cervix uteri, pancreas, gallbladder, capsule tumor, as well as for the stimulation of the cardiac muscle, angiography or even cerebral cartography as non limitative examples.

Furthermore, the skilled addressee will appreciate that the device for orienting may also be used in several types of prosthesis, in devices for movement assistance or even in systems for positioning and maintaining given anatomical structures during clinical interventions.

The device for orienting may be manufactured at a low cost, which is of great advantage for reducing the overall medical costs associated to a clinical intervention.

Although the above description relates to a specific preferred embodiment as presently contemplated by the inventors, it will be understood that the invention in its broad aspect includes mechanical and functional equivalents of the elements described herein.

The invention claimed is:

1. A device for orienting an object according to a given spatial orientation, said device comprising:
    a frame;
    a supporting member adapted for supporting at least a portion of said object, said supporting member being operatively connected to the frame;
    a plurality of elastic fluid actuated devices for displacing the supporting member with respect to the frame, each of said elastic fluid actuated devices having a first end connected to the frame, a second end connected to the supporting member and a deformable hollow body mounted in a prestretched configuration between said first end and said second end, each of said elastic fluid actuated devices being actuatable between a first state wherein the elastic fluid actuated device has a first length and a second state wherein the device has a second length longer than the first length and wherein the first length is a deflated position and the second length is an inflated position, said elastic fluid actuated devices each acting as a compliant elastic element and said plurality of elastic fluid actuated devices defining an overconstrained system, wherein the plurality of elastic fluid actuated devices is adapted to enable an elastically averaged positioning of the supporting member; and an actuation mechanism comprising a plurality of actuating valves, each being respectively operatively connected to a corresponding elastic fluid actuated device for actuating said corresponding elastic fluid actuated device between said first state and said second state;

wherein an actuation of at least one of said elastic fluid actuated devices by said actuation mechanism enables to displace the supporting member with respect to the frame to achieve an equilibrium position for said supporting member which minimizes a potential conservation energy of said device, said equilibrium position being defined by said states of said elastic fluid actuated devices in said overconstrained system, thereby orienting said object according to said given spatial orientation.

2. The device for orienting an object according to claim 1, wherein each of the elastic fluid actuated devices comprises a binary elastic fluid actuated device.

3. The device for orienting an object according to claim 1, wherein the frame has a circular hollow shape, the supporting member being mounted inside the frame.

4. The device for orienting an object according to claim 1, wherein said device for orienting is Magnetic Resonance Imaging (MRI) compatible.

5. The device for orienting an object according claim 1, wherein each of the actuating valves comprises a Dielectric Elastomer Actuator (DEA).

6. The device for orienting an object according to claim 1, wherein each of the actuating valves comprises a piezo-electric actuator.

7. The device for orienting an object according to claim 1, wherein each of the actuating valves comprises a bistable valve and wherein the actuation mechanism is pneumatically actuated.

8. The device for orienting an object according to claim 1, wherein each of said elastic fluid actuated devices is mounted on a given plane for displacing said supporting member on said plane.

9. The device for orienting an object according to claim 8, further comprising an additional plurality of elastic fluid actuated devices arranged on a second plane spaced-apart from the given plane and an additional supporting member mounted on the second plane for supporting at least another portion of said object.

10. The device for orienting an object according to claim 9, wherein said plurality of elastic fluid actuated devices comprises from 2 to 24 devices and said additional plurality of elastic fluid actuated devices comprises from 2 to 24 devices.

11. The device for orienting an object according to claim 1, wherein the frame, the supporting member, the plurality of elastic fluid actuated devices and the actuation mechanism are made from non-electrically conducting materials.

12. The device for orienting an object according to claim 1, wherein the frame, the supporting member, the plurality of elastic fluid actuated devices and the actuation mechanism are made from polymer materials.

13. The device for orienting an object according to claim 1, wherein each of the elastic fluid actuated devices comprises an upper rigid fixture, a lower rigid fixture and wherein said deformable hollow body is mounted between said upper rigid fixture and said lower rigid fixture, said deformable hollow body comprising a hyper-elastic material selected from a group consisting of polyurethane rubber, silicon, acrylic and natural rubber.

14. The device for orienting an object according to claim 13, wherein the hyper-elastic material comprises a low viscoelastic material.

15. The device for orienting an object according to claim 1, further comprising a control unit operatively connected to the actuation mechanism for controlling the actuation of each of said elastic fluid actuated devices, the device for orienting further comprising a position sensor operatively connected to the control unit for sensing an actual position of at least one of the supporting member and a tip of the object.

16. The device for orienting an object according to claim 1, wherein the plurality of elastic fluid actuated devices is operatively connected between the frame and the supporting member and is adapted to enable an elastically averaged positioning of the supporting member.

17. The device for orienting an object according to claim 1, wherein the object comprises a medical device.

18. The device for orienting an object according to claim 1, wherein the object comprises a medical device for insertion of a therapeutic agent into an anatomical structure, said therapeutic agent being selected from a group consisting of a radioactive material, a cryogenic agent and a chemotherapy agent.

19. A method for attaining a given target with an object in an anatomical structure, the method comprising:
    providing an object and a device for orienting the object according to a given spatial orientation as claimed in claim 1, such that the target is extending proximate the device for orienting the object;
    installing the object on the device for orienting the object according to a given spatial orientation;
    actuating the actuation mechanism of the device for orienting the object such that the object attains the given target.

* * * * *

UNITED STATES PATENT AND TRADEMARK OFFICE
CERTIFICATE OF CORRECTION

| | |
|---|---|
| PATENT NO. | : 9,068,576 B2 |
| APPLICATION NO. | : 13/207599 |
| DATED | : June 30, 2015 |
| INVENTOR(S) | : Jean-Sebastien Plante et al. |

It is certified that error appears in the above-identified patent and that said Letters Patent is hereby corrected as shown below:

In Item No. (73), on the title page of the issued US patent, the Assignee name should read as follows:

-- SOCPRA SCIENCES ET GENIE S.E.C. --

Signed and Sealed this
Twenty-third Day of August, 2016

Michelle K. Lee
*Director of the United States Patent and Trademark Office*